United States Patent [19]

Suzuki et al.

[11] Patent Number: 4,730,902

[45] Date of Patent: Mar. 15, 1988

[54] INFRARED ABSORBENT

[75] Inventors: Yoshiaki Suzuki; Gouichi Hayashi, both of Minami-ashigara, Japan

[73] Assignee: Fuji Photo Film Co., Ltd., Kanagawa, Japan

[21] Appl. No.: 895,952

[22] Filed: Aug. 13, 1986

[30] Foreign Application Priority Data

Aug. 13, 1985 [JP] Japan ................. 60-178325

[51] Int. Cl.$^4$ .......................... F21V 9/04; G02B 5/20; C07F 11/00; C07F 9/00
[52] U.S. Cl. ................................. 350/311; 252/587; 350/353; 546/2
[58] Field of Search ................ 252/587, 582; 350/353, 350/311; 546/2

[56] References Cited

U.S. PATENT DOCUMENTS

| | | | |
|---|---|---|---|
| 3,588,216 | 6/1971 | Bloom | 252/587 X |
| 3,687,862 | 8/1972 | Bloom | 252/587 |
| 3,724,934 | 4/1973 | Bloom | 252/587 |
| 3,806,462 | 4/1974 | Bloom | 252/587 |
| 3,895,199 | 4/1975 | Bloom | 252/587 X |
| 4,062,867 | 12/1977 | Bloom | 252/587 X |

FOREIGN PATENT DOCUMENTS

| | | | |
|---|---|---|---|
| 57-021458 | 2/1982 | Japan | 252/587 |
| 61-011704 | 1/1986 | Japan | 252/587 |
| 61-042585 | 1/1986 | Japan | 252/587 |

OTHER PUBLICATIONS

Epstein et al., "Möbauser Spectra of Tin Dithiolates", J. Inorg. Chem., vol. 4, No. 11, Nov. 1965, pp. 1551–1554.
Bustos et al., "Neutral and Anionic Derivatives of Toluene-3,4-Dithiolatocadmium (II) . . . ", in Can. J. Chem., V. 61, 1983, 1146–1152.
Douek et al., "Some Dithiolatotitanium Compounds", J. Inorg. Nucl. Chem. 1977, V. 39, pp. 1470–1472.

*Primary Examiner*—John F. Terapane
*Assistant Examiner*—Catherine S. Kilby
*Attorney, Agent, or Firm*—Birch, Stewart, Kolasch and Birch

[57] ABSTRACT

An infrared absorbent comprising a metal complex compound prepared by coordinating a thiorato bidentate ligand and a nitrogen-containing bindentate ligand to a center metal. With use of the infrared absorbent, there is provided an infrared absorbing material capable of absorbing a far-infrared or near-infrared light having a wavelength of 700 nm or more, which has a high transmittance of a visible light and a good fastness to heat and light. The infrared absorbing material can be used for an infrared absorbing material such as an optical filter or other various objects.

19 Claims, 3 Drawing Figures

INFRARED ABSORBENT

BACKGROUND OF THE INVENTION (1) Field of the Invention

This invention relates to an infrared absorbent. More specifically this invention relates to a novel infrared absorbent suitable for an optical fiber for absorbing near infrared rays or far infrared rays having a wavelength of 700 nm or more.

(2) Description of the Prior Art

Heretofore, various applications of an infrared absorbing material capable of selectively absorbing rays of a far infrared light of a near infrared light having a wavelength of 700 nm or more has been proposed. The following is five examples of conventional primary applications of the infrared absorbing material.

(1) Safelight filter for infrared-sensitive materials:

Recently, there have been developed many silver halide light sensitive materials (which will be hereinafter referred to as "light sensitive materials") which are sensitive to rays of a far infrared light or a near infrared light having a wavelength of 700 nm or more. That is, light sensitive materials are made to have an infrared sensitivity irrespective any distinction between black and white photographs or color photographs including a normal-type, instant-type and thermal developed-type photographs. These materials are useful for an artificial color photograph for resource search or to be exposable with a light emission diode capable of emitting a light in an infrared area.

Conventionally, a safelight filter for a panchromatic photosensitive material has been used as such infrared-sensitive materials.

(2) Control of growth of plants:

It has been long known that a so-called morphogenesis with regard to the growth and differentiation of plants such as the germination of a seed, the extension of a stem, the development of a leaf, the budding of a flower and the formation of tuber is influenced by light, and it has been studied as a photomorphogenesis.

If a plastic film capable of selectively absorbing rays having a wavelength of 700 nm or more is obtainable, it will be possible to control a spectral energy distribution of a light to adapt the above-mentioned principle to an actual productive cite, thereby providing a great progress and profit to an equipped agriculture site. For example, it is expected that earing time may be delayed or growth may be controlled by covering plants with a near-infrared absorbing film at a specific time to cut-off light having a wavelength of 700 nm or more. (See "Chemical Control of Plants", Katsumi Ineda, Vol. 6, No. 1 (1971))

(3) Cut-off of heat radiation:

Solar radient energy rays of a near infrared and an infrared area having a wavelength of 800 nm or more is absorbed by an object and converted to a thermal energy. In addition, a large part of its energy distribution is converged at a near infrared area having a wavelength of 800–2000 nm. Accordingly, a film capable of selectively absorbing rays of a near infrared light is remarkably effective for the cut-off of solar energy, and it is possible to suppress an increase in temperature in a room admitting visible light. Such a film may be adapted to a window of a house, office, store, automobile and airplane, etc. as well as a gardening green house. In particular, as to the green house, temperature control is very important, and if temperature is excessively elevated, plants will be greatly damaged which will finally result in withering. Accordingly, when the near infrared absorbing film is used, the temperature control may be rendered easy, and a new technique such as retarded cultivation in summer may be developed. A conventional heat radiation cutting-off material includes a thin metallic layer deposited on a surface of a plastic film or an inorganic compound, e.g., FeO dispersed in a glass.

(4) Cut filter of infrared rays noxious to tissues of human eyes:

Infrared rays contained in sun light or in light radiated by welding have a harmful influence to the tissues of human eyes. One of the primary applications of the infrared cut filter is an application to spectacles for protecting the human eyes from rays of light containing such harmful infrared rays, e.g., sunglasses and protecting glasses in welding.

(5) Infrared cut filter for a semiconductor light receiving element:

In another field where development of this kind of infrared absorbing plastics is most intensively desired, the infrared absorbing plastics are adapted to an infrared cut filter for a photosensor to make the spectral sensitivity of a semiconductor light receiving element such as silicon photo diode (which will be hereinafter referred to as SPD) approach to a relative spectral sensitivity curve.

Figure 2:
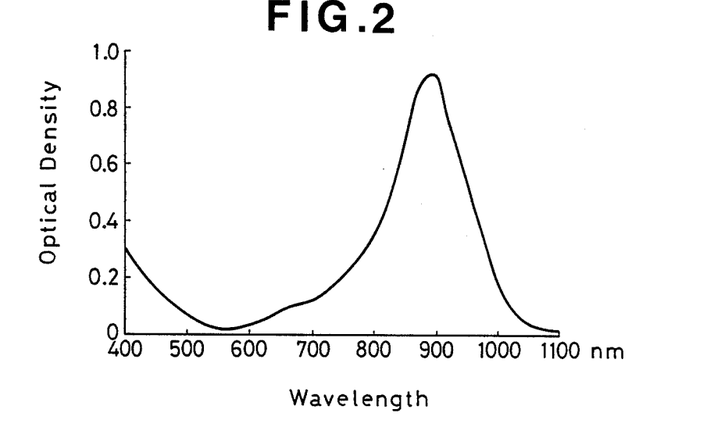
Figure 3:
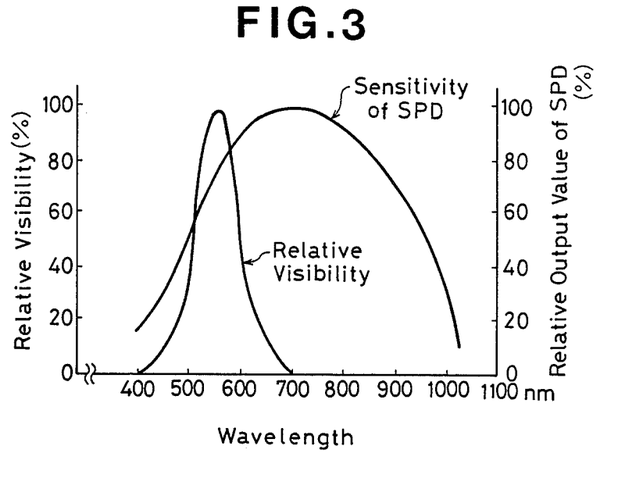
FIG. 3 is a graphical representation showing a relative sensitivity of each of human eyes and an SPD with respect to the wavelength of light.

Presently, SPD is mainly used as a light receiving element of a photosensor used in an automatic exposure meter for a camera or the like. FIG. 2 shows a graph of the relative spectral sensitivity curve and that of a relative value of an output of SPD to each wavelength.

In order to use SPD for an exposure meter, it is required to cut-off light in an infrared area which is not sensitive to human eyes and to make the spectral sensitivity curve of SPD shown in FIG. 2 approach the relative spectral sensitivity curve. Particularly, as an output of SPD is large to the light having a wavelength of 700–1100 nm, and the eyes are insensitive to such a light, this is one of factors of malfunction of the exposure meter. Therefore, if it is possible to use an infrared absorbing plastic film suppressing an absorption of a visible light area, while permitting an absorption of an infrared light area in the entire range of 700–1100 nm, light transmittance in a visible area may be increased and an output of SPD may also be increased. Thus, it will be possible to apparently remarkably improve the performance of the exposure meter.

Conventionally, this kind of photosensor has been practically used by mounting an infrared cut filter made of glass containing an inorganic infrared absorbent to a front surface of SPD.

Moreover, in general the organic dyestuff infrared absorbents in the prior art are almost always unsatisfactory in practical use because of their low light fastness and heat fastness.

Further, regarding the above-mentioned applications, filter materials as used have the following shortcomings.

The safelight of filter for the panchromic photosensitive material in the afore-mentioned applications (1) permits a green light having a high luminosity factor to be partially transmitted, and also permits a large quantity of infrared light to be transmitted in cause fogging. For this reason, such a safelight filter has not been able to achieve its object for infrared sensitive materials.

In the applications (3), the metallic layer deposited plastic film or the FeO dispersed glass functions to intensively absorb not only infrared light but also visible light to cause reduction in inside luminance. For this reason, such a plastic film or glass is not suitable for agricultural uses because of the lack of an absolute quantity of sunshine. Especially, the filter material for growth control of plants in the applications (2) is required to selectively absorb a light having a wavelength of 700-750 nm, and therefore the metallic layer deposited film is quite unsuitable for such an object.

Furthermore, in the applications (5), the infrared cut filter using the infrared absorbent containing an inorganic substance is relatively fast to heat and light, but light transmittance in a visible area is low. To cope with this, the sensitivity of SPD was intended to be increased. However, an increase in the sensitivity of SPD results in an increase in leak current to cause a malfunction of the photosensor, resulting in a big problem in reliability. Additionally, since the infrared cut filter contains an inorganic substance, there is a lack in the flexibility in the production of a photosensor and a difficulty in improving the production process. Further, the infrared cut filter containing an inorganic substance causes a high production cost which results in a great increase in the cost of the photosensor.

In this manner, although the photosensor using the conventional cut filter containing an inorganic substance has a spectral sensitivity similar to the spectral luminous efficiency curve, it has a remarkable defect in such a viewpoint as a reduction in the operational performance, an increase in the production cost and a difficulty in improving the production process.

Moreover, the conventional near-infrared absorbing plastic film containing the infrared absorbent of a complex containing quaternary ammonium group does not have a sufficient solubility of the infrared absorbent to an organic solvent, which was a restriction in preparing a thin plastic film layer.

In other words, the SPD filter as mentioned above is desired to have a very small thickness and a good absorption efficiency of infrared rays. To this end, it is necessary to disperse a large quantity of infrared absorbent in resin. Therefore, the infrared absorbent having a small solubility to an organic solvent has not met the above requirements.

Furthermore, a conventional near-infrared absorbing plastic film containing a metal complex as an infrared absorbent has a soft wavelength of absorption maximum, and therefore it was unsuitable for application to a light receiving element of a semiconductor laser which is increasing its uses.

SUMMARY OF THE INVENTION

Accordingly, it is an object of the present invention to provide an infrared absorbent which has absorption maximum in a long wavelength region, particularly, at 700 nm or more, more particularly at 700 nm to 2600 nm.

It is another object of the present invention to provide a near infrared absorbent which has high solubility in an organic solvent and good compatibility with a film forming binder.

It is a further object of the present invention to provide an infrared absorbent composition containing an infrared absorbent having absorption maximum in a long wavelength region, particularly, at 700 nm or more.

It is still a further object of the present invention to provide an infrared absorbent which can be employed for various applications including the aforementioned applications, that is, for a safelight filter for infrared sensitive materials, control of growth of plants, cut-off of heat radiation, infrared cut filter harmful to tissues of human eyes, infrared cut filter for semiconductor light receiving elements or color solid image pick-up elements, and infrared cut filter for an optelectronic integrated circuit wherein electrical and optical elements are incorporated in the same substrate.

Other and further objects, features and advantages of the invention will appear more fully from the following description taken in connection with the accompanying drawings.

DETAILED DESCRIPTION OF THE INVENTION

It has been found that the above-described objects are, effectively accomplished by an infrared absorbent comprising at least one of compounds represented by the following general formula:

wherein M represents a nickel, palladium or platinum; $R^1$, $R^2$, $R^3$, $R^4$, $R^5$, $R^6$, $R^7$ and $R^8$, which may be the same or different one another such independently represents a hydrogen atom, a halogen atom, an alkyl group, an alkoxy group, an alkoxycarbonyl group, or a substituted or unsubstituted phenyl group; each pair of $R^1$ and $R^2$, $R^2$ and $R^3$, $R^3$ and $R^4$, $R^4$ and $R^5$, $R^5$ and $R^6$, $R^6$ and $R^7$, and $R^7$ and $R^8$ may be bonded to each other to form a ring; and $R^9$, $R^{10}$, $R^{11}$ and $R^{12}$ each represents a hydrogen atom, a halogen atom, a substituted or unsubstituted alkyl group, a substituted or unsubstituted alkoxy group, or a substituted or unsubstituted amino group and may be the same or different from one another.

Further, the present invention provides an infrared absorbent composition and material comprising at least one of the compounds represented by the above-described general formula.

Now, the present invention will be described more detailedly hereinafter.

In the compounds represented by the above-described general formula, the alkoxycarbonyl groups represented by $R^1$, $R^2$, $R^3$, $R^4$, $R^5$, $R^6$, $R^7$ and $R^8$ preferably contain 2 to 19 carbon atoms and may be branched or straight chain. Also, the alkoxycarbonyl groups may be substituted or unsubstituted. The alkoxycarbonyl groups may include, for example, a methoxycarbonyl group, ethoxycarbonyl group, butoxycarbonyl group, n-decyloxycarbonyl group, n-hexadecyloxycarbonyl group and the like.

Examples of the substituted or unsubstituted phenyl groups represented by $R^1$, $R^2$, $R^3$, $R^4$, $R^5$, $R^6$, $R^7$ and $R^8$ may include a phenyl group, sulfophenyl group, carboxyphenyl group and the like.

The halogen atoms represented by $R^1$ to $R^8$, $R^9$, $R^{10}$, $R^{11}$ and $R^{12}$ include fluorine, chlorine, bromine and iodine.

The substituted or unsubstituted alkyl groups represented by $R^1$ to $R^8$, $R^9$, $R^{10}$, $R^{11}$ and $R^{12}$ are preferably those containing 1 to 20 carbon atoms, which may be branched or straight chain. Accordingly, the alkyl groups include a methyl group, ethyl group, propyl group, butyl group, hexyl group, 2-ethylhexyl group, octyl group, decyl group, dodecyl group, hexadecyl group, octadecyl group and the like.

The alkyl group represented by each $R^1$ to $R^8$ is preferably a lower alkyl group containing 1 to 4 carbon atoms, and more preferably, is a methyl group.

Examples of the substituted or unsubstituted alkoxy groups represented by $R^1$ to $R^8$, $R^9$, $R^{10}$, $R^{11}$ and $R^{12}$ include a methoxy group, ethoxy group, propyloxy group, butoxy group, 2-ethylhexyloxy group, n-decyloxy group, n-dodecyloxy group, n-hexadecyloxy group and the like.

Examples of the substituted or unsubstituted amino groups represented by $R^9$, $R^{10}$, $R^{11}$ and $R^{12}$ include an amino group, N-methylamino group, N,N-dimethylamino group and the like.

Each pair of $R^1$ and $R^2$, $R^2$ and $R^3$, $R^3$ and $R^4$, $R^4$ and $R^5$, $R^5$ and $R^6$, $R^6$ and $R^7$, and $R^7$ and $R^8$ may bond together to form a five-membered or six-membered ring, which may be substituted or unsubstituted and may be condensed (e.g. a benzene ring, a naphthalene ring).

The central metal M in the above-described general formula is preferably a nickel from the economical standpoint, but in the light of a molecular absorption coefficient, the metal M is preferably a palladium and most preferably is a platinum.

Now, preferred compounds represented by the above-described general formula will be exemplified hereinafter, but the present invention should not be construed as being limited thereto.

Exemplified Compound

(1)

Exemplified Compound (2)

(3)

(4)

(5)

(6)

(7)

-continued

Exemplified Compound (8)

(9)

(10)

(11)

(12)

-continued

Exemplified Compound (13)

(14)

(15)

(16)

(17)

-continued
Exemplified Compound (18)

Absorption maximums (λmax: nm) of the typical exemplified compounds are shown in Table below.

| Compound No. | λmax (nm) |
| --- | --- |
| (1) | 702 |
| (2) | 712 |
| (3) | 730 |
| (4) | 750 |
| (5) | 716 |
| (6) | 905 |
| (7) | 892 |
| (8) | 902 |
| (9) | 895 |
| (10) | 892 |
| (11) | 912 |
| (12) | 911 |
| (13) | 830 |
| (17) | 898 |
| (18) | 900 |

SYNTHESES EXAMPLES

An infrared absorbent of the present invention can be prepared according to procedures described in Journal of Inorganic and Nuclear Chemistry, Vol. 29, p. 1047 (1967).

More particularly, the infrared absorbent was obtained by dissolving anhydrous (NN)$_2$NiX$_2$ ((NN): nitrogen-containing ligand; X: halogen, nitrate ion or the like) in methanol and then adding benzene-1,2-dithiol or its derivative thereto.

Synthesis 1

(Synthesis of exemplified compound No. 7)

The synthesis was carried out according to the procedures disclosed in the above-described reference.

20 g of bis-orthophenanthroline nickel chloride was dispersed in 400 ml of methanol and 8 g of toluene-3,4-dithiol was then added thereto at a room temperature while stirring, so that black precipitate was immediately formed. The stirring was further continued for one hour and the filtration was carried out to obtain the precipitate, which was then washed with methanol and air-dried. The dried product was subjected to recrystallization in methylene chloride. Yield 21 g, λmax 892 nm, εmax $0.83 \times 10^4$ lmol$^{-1}$cm$^{-1}$.

Synthesis 2

(Synthesis of exemplified compound No. 10)

The compound was also prepared according to the above-described reference.

13.1 g of bis-(2,2'-biquinoline)nickel chloride was dispersed in 200 ml of methanol and 4.0 g of toluene-3,4-dithiol was then added thereto at a room temperature, so that black precipitate was formed immediately. Then, the stirring was further continued for one hour and then the filtration was carried out to obtain the precipitate. The precipitate was washed and air-dried and finally subjected to recrystallization from methylene chloride. Yield 12 g, λmax 892 nm, εmax $1.3 \times 10^4$ lmol$^{-1}$cm$^{-1}$.

Other exemplified compounds suitable for use in the present invention can be synthesized according to the same manner as described in Synthesis 1 or 2.

In the following, there will be described the preparation of the infrared rays absorbing composition and absorbing material of the invention.

The infrared absorbent of the present invention may be used by allowing it to be contained in a suitable binder or be coated on a suitable support. The binder may be any organic and inorganic materials capable of exhibiting an infrared absorbing property, which materials may be high molecular materials such as plastics or inorganic materials such as glass, for example.

The binder is preferably capable of forming a film which is superior in transparency and mechanical property. Examples of such a film forming binder may include polyesters such as typically polyethylene terephthalate, cellulose esters such as cellulose acetate, cellulose triacetate and cellulose acetate butylate, polyolefins such as polypropylene, polyvinyl compounds such as polyvinyl chloride, polyvinylidene chloride, vinyl chloride-vinyl acetate copolymer, and polystyrene, acrylic addition polymers such as polymethyl methacrylate, polycarbonates such as polycarbonic acid ester, phenol resin, urethane resin or gelatin as a known hydrophilic binder.

As one of methods of forming a film by adding the infrared absorbent to the above-mentioned plastic materials or incorporating the same with the plastic materials, the infrared embodiment is incorporated in the plastics before preparing the film. Namely, the infrared absorbent is mixed with a polymer powder or pellet together with various additives, and is molten to extrude the mixture by a T-die process or a tubular film process, or make the mixture into a film by calendering thereby to give a film containing the absorbent as uniformly dispersed. In the case of preparing the film from a polymer solution by a casting method, the infrared absorbent may be contained in the polymer solution.

In a second method, an infrared absorbing layer may be formed by applying a polymer solution or dispersion containing the infrared absorbent onto a surface of various plastic films or glass plates as prepared by a suitable method. A binder polymer used for a coating liquid is selected from materials having a good solubility of the infrared absorbent and a superior adhesiveness to the plastic film or glass plate as a support. For example, a suitable one of these materials may be polymethyl methacrylate, cellulose acetate butylate, or polycarbonate. Optionally, a suitable undercoat may be preliminarily formed on the support film for purpose of improving adhesiveness.

In a third method, a filter may be formed in a frame of a light window of an element to be isolated from infrared rays with use of a polymer prepared by mixing the infrared absorbent with a polymerizable monomer and adding a suitable polymerization initiator to polymerize the mixture with heat or light. In this method, the element may be entirely enclosed by plastics as prepared from ethylene unsaturated polymerizable monomer or addition polymerizable composition such as epoxy resin.

In a fourth method, the infrared absorbent may be deposited by evaporation on a suitable support. In this method a suitable film forming binder layer as a protective layer may be formed on the deposited layer.

A method of utilizing the near-infrared absorbent of the present invention for a color solid image pick-up element is as follows:

(1) A plurality of striped or mosaic color separation filter layers having predetermined spectral characteristics are formed, and then the near-infrared absorbent is incorporated in a surface protective layer to be formed on the filter layers, or the absorbent is deposited on the surface protective layer.

(2) The near-infrared absorbent of the present invention in combination with a visible light absorbing dyestuff may be incorporated in the color separation filter layers.

(3) The near-infrared absorbent may be incorporated in a transparent intermediate layer or a surface smooth layer provided in a multi-layer color separation filter.

An optical filter obtained by combining the infrared embodiment of the present invention with a suitable binder is especially effective when it is used in combination with color separation filters as described in Japanese Patent Application (OPI) Nos. 58107/82, 9317/84 and 30509/84.

In preparing an infrared absorbing material with use of the infrared absorbent of the present invention, two or more of the infrared absorbent may be used in combination. Further, a known near-infrared absorbent of organic or metal complex substance may be used in combination. Particularly, when an absorbent having an absorption maximum different from that of the absorbent of the invention is used in combination, a range of absorption wavelength may be widened.

It is effective to add an ultraviolet absorbent to the infrared absorbent in the infrared absorbing material for purpose of improving a light fastness. Examples of the ultraviolet absorbent may include substituted or unsubstituted benzoates such as resorsin monobenzoate and methyl salicyclate, cinnamates such as 2-oxy-3-methoxy cinnamate, benzophenones such as 2,4-dioxy-benzophenone, $\alpha,\beta$-unsaturated ketones such as 2,4-dibenzal acetone, coumarins such as 5,7-dioxy-coumarin, carbostyrils such as 1,4-dimethyl-7-oxycarbostyril, or azoles such as 2-phenyl benzoimidazole and 2-(2-hydroxyphenyl)benzotriazole.

In case of a film prepared by a coating method in combination of the infrared absorbent of the invention with a suitable binder, a thin plastic film may be attached or coated on a surface of the coating layer for purposes of protectin or providing anti-stick quality. For example, a laminated film may be obtained by laminating a polyvinyl chloride film having a thickness of 0.05 mm on the coating layer and heat-bonding the whole at 120°-140° C.

In preparing the optical filter material from the infared absorbent of the present invention, 0.1-50 parts by weight, preferably 0.5-10 parts by weight of the infrared asorbent is contained in 100 parts by weight of the binder. An optical filter is obtained by working and treating the optical filter material so as to have a sufficient degree of transmittance in a wavelength range where infrared rays are to be cut-off. Accordingly, it is necessary to adjust a content of the compounds with respect to the binder and a thickness of the filter, so as to obtain a transmittance of 10% or less, preferably 2.0% or less, and more preferably 0.1% or less in the wavelength range of 900 nm or more at the trough of a transmittance curve. Although a practical thickness of the filter is in the range of 0.002 mm to 0.5 mm, it is possible to employ any filters having a thickness out of the above range according to applications.

According to the present invention, it is possible to obtain a near-infrared absorbent having an absorption maximum wavelength of about 700 nm or more and having high solubility in an organic solvent and good compatibility with a film forming binder.

Further, it is possible to adjust the absorption maximum wavelength by properly selecting the center metal in the compound represented by the general formula above-described.

According to the present invention, it is possible to provide an optical filter having good fastness to heat and light with relatively low cost.

Further, according to the infrared absorbent of the present invention, it is possible to adjust solubility of the absorbent to a solvent by suitably selecting and combining the ligand and the counter ion in the infrared absorbent of organic metal complex. Accordingly, various binders may be widely utilized in preparing the infrared absorbing material.

The infrared absorbent of the present invention can be applied to various uses including the afore-mentioned applications, that is, for a safelight filter for infrared sensitive materials, control of growth of plants, cut-off of heat radiation, cut filter of infrared rays harmful to tissues of human eyes, cut filter of infrared rays for semiconductor light receiving elements or color solid image pick-up elements, and cut filter of infrared rays for an optelectronic integrated circuit, electrical and optical elements being incorporated in the same substrate.

Moreover, the infrared absorbent of the present invention is variously adaptable according to its infrared absorbing characteristics. For example, when the infrared absorbent is added to a jet printer ink as described in Japanese Patent Application (OPI) No. 135568/81, a reading efficiency by near-infrared rays may be improved, and further it is applicable to a laser recording/reading medium as described in Japanese Patent Application (OPI) No. 11090/82. The infrared absorbent according to the present invention has such a property as of converting absorbed near-infrared rays to heat, and therefore it may be utilized as an infrared rays/heat exchanger. Typical examples of such a converter are as follows:

(1) The infrared absorbent is added to a laser heat sensitive recording material as described in Japanese Patent Application (OPI) Nos. 14095/82 and 14096/82, and an infrared laser is irradiated to the composition to generate heat, thereby enhancing a mixed coloring reaction.

(2) The infrared absorbent may be contained in a regist material as described in Japanese Patent Application (OPI) No. 40256/82 which material may change solubility by a thermal function due to a laser.

(3) The infrared absorbent may be incorporated in a thermodrying or thermosetting composition as described in Japanese Patent Application (OPI) No. 143242/81 to promote reaction.

Furthermore, the infrared absorbent of the present invention may be utilized for an electrophoto sensitive film for an electrophoto printer using a semiconductor laser as a light source as described in Japanese Patent Application (OPI) No. 214162/83, and may also be utilized for an optical disc film which permits writing and reproducing by a semiconductor laser.

It should be noted that applications of the infrared absorbent of the present invention are not limited to the above description.

To further illustrate the present invention and not by way of limitation the following examples are given. Throughout the examples, percentages and ratios are by weight.

Example 1

Infrared absorbents according to the present invention were prepared using exemplified compounds Nos. 7 and 10 synthesized according to the above-described Syntheses 1 and 2 and then an optical filter was formed of each of the so-prepared infrared absorbents.

Constituents of each of Compositions 1 and 2 described below was mixed together, and stirred well and after filtration, the composition was applied to a metal substrate according to a film casting method to form a film, which was then peeled to give an optical filter. This procedure was substantially repeated to prepare several such optical filters each having a thickness varied at a range between 0.02 mm and 0.3 mm.

Composition 1

| | |
|---|---|
| TAC (Cellulose triacetate) | 170 parts |
| TPP (Triphenyl phosphate) | 10 parts |
| Methylene chloride | 800 parts |
| Methanol | 160 parts |
| Exemplified compound No. 7 | 0.7 part |

Composition 2

| | |
|---|---|
| TAC (Cellulose triacetate) | 170 parts |
| TPP (Triphenyl phosphate) | 10 parts |
| Methylene chloride | 800 parts |
| Methanol | 160 parts |
| Exemplified compound No. 10 | 0.7 part |

Figure 1:
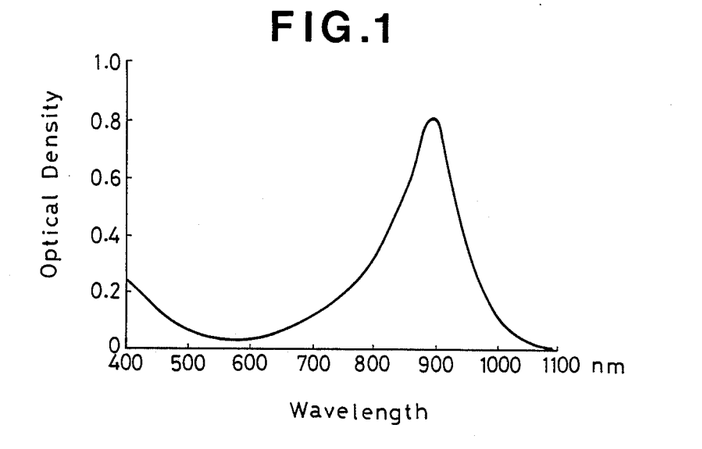
FIGS. 1 and 2 each are a graphical representation showing an optical density of an optical filter material prepared using an infrared absorbent according to the present invention.

Spectral transmittance of optical filters 1 and 2 formed of Compositions 1 and 2 were as shown in FIGS. 1 and 2, respectively. The filters 1 and 2 each had a thickness of 0.1 mm.

Example 2

Example 1 was substantially repeated to prepare an optical filter containing an ultraviolet absorbent and having a thickness of 0.19 mm. A flow casting composition therefor was as follows:

| | |
|---|---|
| TAC (Cellulose triacetate) | 170 parts |
| TPP (Triphenyl phosphate) | 10 parts |
| Methylene chloride | 800 parts |
| Methanol | 160 parts |
| Exemplified compound No. 7 | 2 parts |
| 2-(5-t-butyl-2-hydroxyphenyl)-benzotriazole | 0.2 part |

Example 3

An optical filter (thickness: 0.05 mm) prepared in Example 1 was mounted on a silicon photodiode as a near-infrared cut filter. It was found that a photo detector using the silicon photodiode was highly increased in operational performance. Also, the operational reliability was not varied even after it was subjected to a forced aging test at 50° C.

Further, it was found that a combination of the metal complex of the present invention with an ultraviolet absorbent remarkably improves a light resistance of the filter. The light resistance of an optical filter, prepared by combining exemplified compound No. 12 and ultraviolet absorbent, 5-(5-t-butyl-2-hydroxyphenyl)benzotriazole (Compound (U)) at a ratio of 10:1, are shown in the table below by variation of optical density of the filter under irradiation of light with time.

| | Xenon lamp (120,000 lux) irradiation time (hour) | |
|---|---|---|
| Compound in filter | 0<br>892 nm | 24<br>892 nm |
| Exemplified compound No. 7 | 1.00 | 0.64 |
| Exemplified compound No. 7 + Compound (U) | 1.00 | 0.87 |

As can be seen from the table listed above, the combination of the compound of the present invention with the ultraviolet absorbent much improved the lightfastness of the optical filter.

Example 4

| | |
|---|---|
| Exemplified compound No. 10 | 1 g |
| nitrocellulose | 0.7 g |
| dichloromethane | 30 ml |

A solution having the above-described composition was coated with rotation coating on a glass plate, and dried at 40° C. to give a recording layer having a thickness of 0.40 μm. A reflectance and absorptivity at the wavelength of 830 nm were 15% and 65%, respectively.

In the thus obtained recording medium, a signal was recorded with a semiconductor laser beam at 1 MHz having a wavelength of 830 nm, an energy of 4 mW on an irradiated surface and a diameter of 1.6 μm. A pit having a diameter of 1.0 μm was formed with irradiation (1.2 nJ/pit) of 0.3 μsec. The obtained recording medium was stored at a temperature of 60° C. and a humidity of 90% under an interior light for one month. After the storage, recording and reading characteristics of the recording medium were not changed.

Having described a specific embodiment of our bearing, it is believed obvious that modification and variation of our invention is possible in light of the above teachings.

What is claimed is:

1. A compound represented by the formula:

wherein M represents nickel, palladium or platinum; $R^1$, $R^2$, $R^3$, $R^4$, $R^5$, $R^6$, $R^7$ and $R^8$, which may be the same or different from one another, each independently represents a hydrogen atom, a halogen atom, an alkyl group, an alkoxy group, an alkoxycarbonyl group, or a substituted or unsubstituted phenyl group; each pair of $R^1$ and $R^2$, $R^2$ and $R^3$, $R^3$ and $R^4$, $R^4$ and $R^5$, $R^5$ and $R^6$, $R^6$ and $R^7$, and $R^7$ and $R^8$ may be bonded to each other to form a ring; and $R^9$, $R^{10}$, $R^{11}$ and $R^{12}$ each represent a hydrogen atom, a halogen atom, a substituted or unsubstituted alkyl group, a substituted or unsubstituted alkoxy group, or a substituted or unsubstituted amino group, which may be the same or different from one another.

2. The compound as claimed in claim 1, wherein at least one of $R^9$ to $R^{12}$ is an alkyl group.

3. The compound as claimed in claim 2, wherein $R^{10}$ is a methyl group.

4. The compound as claimed in claim 1, wherein at least one pair of $R^1$ and $R^2$, $R^2$ and $R^3$, $R^3$ and $R^4$, $R^4$ and $R^5$, $R^5$ and $R^6$, $R^6$ and $R^7$, and $R^7$ and $R^8$ bonds to each other to form a ring.

5. The compound as claimed in claim 4, wherein $R^4$ and $R^5$ bond to each other to form a benzene ring.

6. The compound as defined in claim 4, wherein $R^1$ and $R^2$, and $R^7$ and $R^8$ bond to each other to form benzene rings, respectively.

7. An infrared absorbent composition containing at least one compound of claim 1.

8. The infrared absorbent composition as claimed in claim 7 wherein at least one of $R^9$ to $R^{12}$ is an alkyl group.

9. The infrared absorbent composition as claimed in claim 7 wherein at least one pair of $R^1$ and $R^2$, $R^2$ and $R^3$, $R^3$ and $R^4$, $R^4$ and $R^5$, $R^5$ and $R^6$, $R^6$ and $R^7$, and $R^7$ and $R^8$ bonds to each other to form a ring.

10. The infrared absorbent composition as claimed in claim 7 further comprising a film forming binder.

11. The infrared absorbent composition as claimed in claim 8, wherein $R^{10}$ is a methyl group.

12. The infrared absorbent composition as claimed in claim 9, wherein $R^4$ and $R^5$ bond to each other to form a benzene ring.

13. The infrared absorbent composition as claimed in claim 9, wherein $R^1$ and $R^2$, and $R^7$ and $R^8$ bond to each other to form benzene rings, respectively.

14. The infrared absorbent composition as claimed in claim 7, further comprising an ultraviolet absorbent.

15. The compound as claimed in claim 1 which has an absorption maximum at 700 nm or more.

16. The compound as claimed in claim 1, wherein the alkoxy-carbonyl groups represented by $R^1$ to $R^8$ contain 2 to 19 carbon atoms and may be branched or straight chain and the alkyl group represented by $R^1$ to $R^8$ contains 1 to 4 carbon atoms.

17. The compound as claimed in claim 1, wherein M is platinum.

18. An optical filter containing at least one compound of claim 1.

19. The optical filter as claimed in claim 18, which comprises 0.1 to 50 parts by weight of said compound contained in 100 parts by weight of a binder.

* * * * *